United States Patent
Zuñiga Cañon et al.

(10) Patent No.: US 12,294,920 B2
(45) Date of Patent: May 6, 2025

(54) METHOD FOR DETERMINING A LEVEL OF CONTAMINATION IN COVERED ZONES AND SYSTEM FOR COLLECTING AND PROCESSING ENVIRONMENTAL INFORMATION

(71) Applicant: Universidad Santiago de Cali, Cali (CO)

(72) Inventors: Claudia Liliana Zuñiga Cañon, Cali (CO); Rafael Asorey Cacheda, Cali (CO); Darryl Alexander Millan Buelvas, Cali (CO); Juan Garcia Haro, Cali (CO); Antonio Javier Garcia Sanchez, Cali (CO); Juan de Dios Largo Ortiz, Cali (CO)

(73) Assignee: Universidad Santiago de Cali, Cali (CO)

( * ) Notice: Subject to any disclaimer, the term of this patent is extended or adjusted under 35 U.S.C. 154(b) by 405 days.

(21) Appl. No.: 17/774,736

(22) PCT Filed: Nov. 6, 2020

(86) PCT No.: PCT/IB2020/060483
§ 371 (c)(1),
(2) Date: May 5, 2022

(87) PCT Pub. No.: WO2021/090271
PCT Pub. Date: May 14, 2021

(65) Prior Publication Data
US 2022/0408232 A1    Dec. 22, 2022

Related U.S. Application Data

(60) Provisional application No. 62/931,238, filed on Nov. 6, 2019.

(51) Int. Cl.
*H04W 4/38* (2018.01)
*H04W 40/22* (2009.01)
*H04W 84/18* (2009.01)

(52) U.S. Cl.
CPC ............ *H04W 4/38* (2018.02); *H04W 40/22* (2013.01); *H04W 84/18* (2013.01)

(58) Field of Classification Search
None
See application file for complete search history.

(56) References Cited

U.S. PATENT DOCUMENTS

| | | | | |
|---|---|---|---|---|
| 2009/0257373 A1* | 10/2009 | Bejerano | ............... | H04W 24/04 370/328 |
| 2015/0379400 A1* | 12/2015 | Tatourian | .............. | H04L 67/535 706/46 |

(Continued)

OTHER PUBLICATIONS

International Search Report for PCT/IB2020/060483 dated Nov. 2, 2021 (4 pages).

(Continued)

*Primary Examiner* — Andre Tacdiran
(74) *Attorney, Agent, or Firm* — Dinsmore & Shohl LLP

(57) ABSTRACT

A method for determining the level of contamination in cities comprising the steps of providing a server, transmitting information from users which report contamination issues by means of a mobile electronic device to the server, providing a wireless sensor network (WSN) for measuring level of contamination, obtaining measured data tagged with a geo-reference tag and a time stamp, and configured for supporting delay-tolerant communications transmitting data measured from sensors to the server, processing data measured and information from users by using big data and machine learning algorithms, and providing reports on contamination levels; and a system for collecting and processing environmental information comprising at least one mobile (Continued)

electronic device, including at least one environmental sensor, at least one wireless communication interface, a geo-location unit, and a storage unit; at least one communication gateway and at least a server for storing and processing the information obtained.

16 Claims, 6 Drawing Sheets

(56) References Cited

U.S. PATENT DOCUMENTS

| | | | |
|---|---|---|---|
| 2018/0054490 A1* | 2/2018 | Wadhwa | G08G 1/0129 |
| 2018/0199968 A1* | 7/2018 | Pratt | A61B 17/823 |
| 2019/0234920 A1* | 8/2019 | Rangel | G08B 21/12 |
| 2019/0261433 A1* | 8/2019 | Turner | H04L 5/00 |

OTHER PUBLICATIONS

Emiliano Miluzzo et al., "CaliBree: A Self-calibration System for Mobile Sensor Networks," Jun. 18, 2007, Conference: Distributed Computing in Sensor Systems, 4th IEEE International Conference, DCOSS 2008, Santorini Island, Greece, Jun. 11-14, 2008.

* cited by examiner

METHOD FOR DETERMINING A LEVEL OF CONTAMINATION IN COVERED ZONES AND SYSTEM FOR COLLECTING AND PROCESSING ENVIRONMENTAL INFORMATION

RELATED APPLICATIONS

The present application is a U.S. National Phase of PCT/IB2020/060483, entitled "METHOD FOR DETERMINING A LEVEL OF CONTAMINATION IN COVERED ZONES AND SYSTEM FOR COLLECTING AND PROCESSING ENVIRONMENTAL INFORMATION" and filed on Nov. 6, 2020, which claims priority from provisional application No. 62/931,238 entitled "systems and methods for collecting and processing environmental information through mobile devices and open data sources" and filed on Nov. 6, 2019, the entire contents of both are incorporated herein in their entireties.

FIELD OF THE INVENTION

This invention generally relates to a method for determining a level of contamination in cities and a system for collecting and processing environmental information, in particular, through sensing devices and open data sources.

BACKGROUND

A Wireless Sensor Network (WSN) is a type of network composed of different devices called nodes. Each node is associated with battery power and has the capability of sensing, communicating, and data processing as well. The fast development of protocols for the Internet of Things (IoT) paradigm and the reduction of costs in electronic devices have driven the popularization of wireless sensor networks in different sectors like agriculture, industries, and cities.

Due to the pollution problems in the main cities around the world, but also in rural areas and even indoors or outdoors spaces (as buildings, offices, coliseums, stadiums, among others), wireless sensor networks have been an economical and promising technology that could provide a solution for the environmental problem by giving real-time monitoring. Currently, there are several solutions for environmental monitoring in the big cities using wireless sensor networks to monitor air pollution or water contamination, but these solutions fail to meet the needs of the industry because the sensors are fixed in some specific locations around the covered zone; therefore, they do not guarantee total coverage of the area. Besides, some environmental issues cannot be sensed or measured by electronic sensors, such as odors or falling ash; therefore, these issues go unnoticed. Other solutions attempt to use social platforms to extract information about the covered zone's environmental problems. Still, these solutions are similarly unable to meet the needs of the industry because the information given by the users on internet platforms may not be reliable.

SUMMARY OF THE INVENTION

The invention relates to a method for determining the level of contamination in a covered zone. The method of the invention comprises the steps of:
  providing a server,
  transmitting information from users who report contamination issues by means of a mobile electronic device to the server,
  providing a wireless sensor network (WSN) for measuring the level of contamination, obtaining measured data tagged with a geo-reference tag and a time stamp, and configured for supporting delay-tolerant communications for mobile electronic devices, which transmits information between them until at least one obtains a connection to the server, generating a delay-tolerant network (DTN),
  transmitting data measured from sensors to the server,
  processing data measured and information from users by using big data and machine learning algorithms, and
  providing reports on contamination levels, preferably, real-time information on contamination levels, historical contamination levels, predictions, and contamination alerts or recommendations could be provided.

The method of the invention could also comprise the step of obtaining data from open sources.

Before providing the wireless sensor network (WSN), the information from users could also be processed for determining locations of covered zone where sensors are more needed. Preferably, the sensors could be placed on personal devices or vehicles.

Additionally, the information from users could be processed for determining truthfulness by checking if data reported by other users are similar.

The connection to the server could be performed by a fixed communication gateway or a mobile communication gateway, such as a Bluetooth gateway.

Also, the data measured and information from users could be stored in different collections in a non-structured format.

The wireless sensor network (WSN) comprise sensors with a certain calibration level. Preferably, the method of the invention could further comprise a step of tagging measured data as a function of said calibration level. More preferably, the method of the invention could also comprise a step of calibrating low-calibrated sensors from the wireless sensor network (WSN) by using data from sensors having a higher level of calibration and/or using data from open sources.

The invention is also referred to a system for collecting and processing environmental information. The system of the invention comprises: at least one mobile electronic device, wherein the mobile electronic devices comprise at least one environmental sensor, at least one wireless communication interface, a geo-location unit, and a storage unit; at least one communication gateway with at least one wireless communication interface and an internet connection, at least one server configured for storing the information obtained and for processing the information stored by following the method of the invention described before.

In particular, the environmental sensor could be a temperature sensor, humidity sensor, particule matter sensor, being preferably a PM10, PM2.5 or a PM1.0, or a gas sensor, and more preferably, could be an ozone sensor and nitrous oxide sensor, carbon dioxide sensor, sulfur dioxide sensor, volatile organic compounds sensor, ammonia sensor, hydrogen sulfide sensor, and carbon monoxide sensor.

The invention is also referred to a method for transmitting contamination data by using a mobile electronic device, the method comprising the steps of:
  receiving a request from one or more server to enroll a wireless sensor network (WSN) for measuring level of contamination as a response to an initial transmission of information from a user reporting contamination issues by means of a mobile electronic device to said one or more server;

attempting to transmit such information to other mobile electronic devices until the mobile device or at least one of the contacted mobile electronic devices obtains a connection to said one or more servers, generating a delay-tolerant network (DTN); and transmitting data tagged with a geo-reference tag and a time stamp measured from sensors of said mobile device directly, or indirectly, by means of other mobile devices, to said server for processing data measured and information from users by using big data and machine learning algorithms, and for providing reports on contamination levels.

Also, the invention relates to a mobile electronic device configured for supporting delay-tolerant communications and suited to perform the method described.

It is desirable to have a system and a method for monitoring the environmental situation of a place in real-time, which can provide reliable and valuable information to the people that live there or stay there for a while. Furthermore, it is desirable to have a system that monitors every kind of contamination in a covered zone and not only air pollution or water contamination that can be measured by electronic sensors. Still, it is desirable to have a system that provides environmental data about all the space inside or indoors for a specific area and not only on fixed points inside the area. The disclosed invention advantageously fills these needs and addresses the aforementioned deficiencies by providing a system for collecting and combining data and a method for determining a level of contamination, preferably coming from different information sources, including a network of mobile electronic devices, a mobile application installed on smartphones and open public databases.

The system is preferably made up of the following components: a network of mobile electronic devices equipped with a plurality of environmental sensors that periodically send measurements to a database; a mobile collaboration application that allows the residents to transmit environmental data to a database; a system that gathers information from open data sources and sends it to a database; and a server that collects the data stored in the database, processes it and provides valuable information to the residents and the local authorities. Also, the invention comprises a method for determining a level of contamination by collecting and processing the multisource information, combining it, and giving useful information to the users, residents, and local authorities, such as information services, recommendations, and forecasts.

The wireless sensor network is composed of a set of mobile electronic devices, called sensor nodes, each optionally having a plurality of environmental sensors, such as temperature sensor, humidity sensor, ozone and nitrous oxide sensor, carbon dioxide sensor, Sulphur dioxide sensor, and carbon monoxide sensor, among other gas sensors. A plurality of communication interfaces and a geo-positioning system, which collects data from the environment and sends it to a communication gateway. Optionally, a sensor node transmits data to another mobile electronic device using at least one communication interface.

The mobile electronic devices with the plurality of sensors may also have an interface, such as a Bluetooth interface, to allow the mobile electronic devices to send data to the database through a Bluetooth gateway, such as a smartphone, when none of the mobile electronic devices or the communication gateway are in the coverage zone. The mobile electronic devices with the plurality of sensors may also have a long-range wireless interface to connect each mobile electronic device directly to the communication gateway, avoiding routing among mobile electronic devices, thereby energy consumption can be reduced in the network. The mobile application may also have a machine learning (ML) algorithm to detect the truthfulness of the reports and avoid incorrect data that could affect the system.

The mobile electronic devices, also called sensor nodes, preferably are portable devices or wearable devices which are carried by the users throughout the covered zone for collecting environmental data. In another embodiment, the sensor nodes are attached to public or private vehicles or transport means like cars, bicycles, motorcycles, buses, or trains that are continuously moving along the monitored zone, providing complete coverage. Additionally, the transport means also provide energy supply to the sensor nodes. However, mobility also implies problems in terms of network connectivity and management. Thus, the present invention also uses a self-organized, delay, and fault-tolerant communication system to guarantee that the data will be transferred to the database.

The self-organized, delay and fault-tolerant communication system is a delay tolerant network (DTN) which can have a topology of a mobile ad-hoc network (MANET). This network architecture assumes that mobile electronic devices will be disconnected most of the time. Therefore, when a mobile electronic device acquires measurements from the environment, it will attempt to transmit the data to another mobile electronic device or attempt to send the data to the communication gateway if it is within the coverage zone. Otherwise, the data will be stored until the mobile electronic device can transmit the measurements successfully. Consequently, all collected data can be transmitted to the database, while sensor nodes move throughout the covered zone.

Finally, the application allows the users to access valuable information and services generated from the data collected and processed by the monitoring system. The mobile app gives different types of environmental reports, including air quality, water quality, garbage, and noise, among others. Users can select the type of report, take a picture, record an audio file or a video file, write a report description, and share their location. All this information will be sent to the database to be stored for later processing. Users can also access reports made by others to make comments or vote. Voting will rank reports for the processing stage to determine the importance and the veracity of the reported problem.

The integration of the data collected from the wireless sensor network (crowdsensing) and the data collected from the users (crowdsourcing) has two main advantages. First, the information provided by users is subjective and may be unreliable. However, WSNs can increase reliability. Second, crowdsourcing enables the system to retrieve data that sensor nodes cannot detect thanks to the capacity of human beings to reason and analyze. Finally, the integration with open data sources increases the reliability and accuracy, reducing the error caused by less accurate sensors.

The disclosed invention is unique when compared to other known systems and solutions in that it provides complete and reliable information about the environmental situation of the covered zone in terms of spatial coverage and type of environmental issues thanks to the combination of multiple sources of information. Preferably, the covered zone is an outdoor space. Optionally, the covered zone is an indoor space. The system can provide real-time information about air pollution or water contamination, among other types of environments, based on sensor measurements, but also information that cannot be sensed like odors, falling ash, and the amount of nanoparticles (as viruses), among others. Furthermore, the mobile electronic devices equipped with the plurality of sensors are calibrated based on the data gathered from open data sources, which usually is data coming from local environmental authorities with high precision devices. Additionally, the reports made by the users are analyzed by an algorithm that validates the truthfulness of the information. These functionalities contrast with the existing systems with only one source of information, which usually is the information measured by a network of sensors.

More specifically, the system is unique due to the sensor network architecture, which is a MANET that uses a DTN stack for transferring the data. This type of architecture is not present in another system for environmental monitoring; typically, the systems for environmental monitoring are composed of stationary sensors which do not allow covering the monitored zone totally.

Furthermore, the system is unique due to the presence of three different means for collecting environmental information: the first, related to a co-creation platform for collecting environmental reports; the second, a mobile network of sensors for measuring environmental variables; and the third, a system for gathering information from open data sources. Finally, the three systems are connected to a processing system with machine learning capabilities, which will generate valuable information based on the collected data. The co-existence of the three means for collecting data, and the combination of the collected data is not present in another system.

BRIEF DESCRIPTION OF THE DRAWINGS

This disclosure will now provide a more detailed and specific description that will refer to the accompanying drawings. The drawings and particular specifications of the drawings, as well as any specific or alternative embodiments discussed, are intended to be read in conjunction with the entirety of this disclosure. The systems and methods for collecting and processing environmental information through mobile devices and open data sources may, however, be embodied in many different forms and should not be construed as being limited to the embodiments set forth herein. Instead, these embodiments are provided by way of illustration only and in order for this disclosure to be thorough, complete, and so that it fully conveys understanding to those skilled in the art.

The illustrations of possible embodiments of the invention are described.

DETAILED DESCRIPTION OF THE INVENTION

Figure 1:
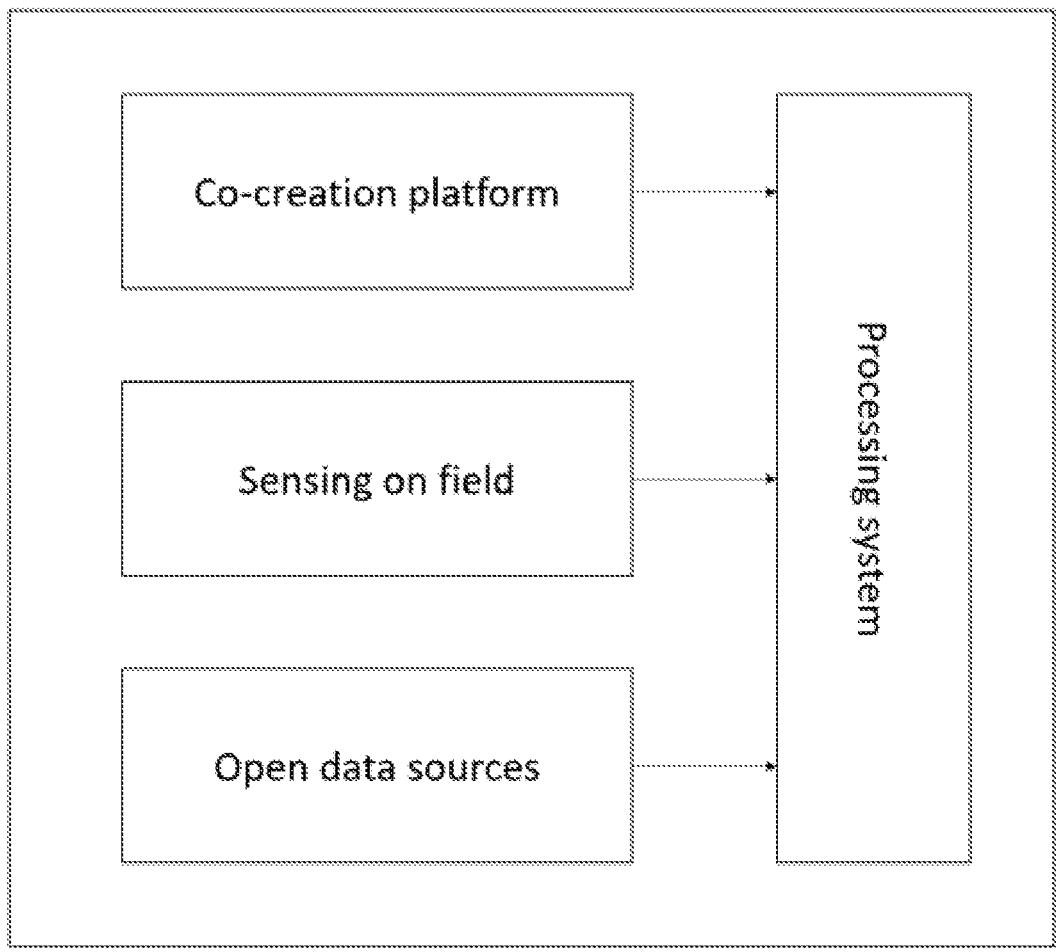
FIG. 1. is an illustration of the general components of the environmental monitoring system according to the present invention.

The present invention is directed to a system for collecting and processing environmental information and a method for determining a level of contamination, preferably, by using mobile devices and open data sources.

A covered zone is defined in the present invention as any indoors or outdoors spaces (as buildings, offices, coliseums, stadiums, among others). The covered zone as outdoor space can be a preferably a city, as indoor space can be a residence. Optionally, the covered zone as outdoor space can also be rural areas, as indoor space can be buildings, offices, coliseums, stadiums, and similar infrastructures.

In an embodiment, the system is made up of at least one and up to all of the following components. At least one mobile electronic device with a plurality of environmental sensors; the mobile electronic device having a geo-location system; a storage unit; a rechargeable battery; and with at least two wireless communication interfaces, one of which is a Bluetooth communication interface.

At least one communication gateway with high computation capabilities, a storage unit and at least one wireless communication interface. The communication gateway is connected to a fixed source of energy due to its high energy consumption.

A self-organized, delay, and fault-tolerant communication system that allows communication among the mobile electronic devices, and the communication of the mobile electronic devices with the communication gateway.

A mobile application installed in at least one mobile device with an internet connection, such as a smartphone, which enables users to send environmental reports to the database with multiple multimedia formats like photos, videos, and audio files. Additionally, the users can see the reports made by other users and vote if they share the same experience. Additionally, the mobile application brings access to information services, environmental alerts, and environmental forecasts to the user, that are generated by processing the information collected by the system.

A short-range wireless communication gateway with an internet connection that allows the mobile electronic devices to send the information to the database when the gateway or other mobile electronic devices are out of range. The short-range wireless communication gateway is preferably a mobile phone with an Internet connection and with the mobile application installed on it.

A system for gathering information from open data sources that takes the data and pre-processes it by deleting non-valid or null fields, and then sends it to the database through an Internet connection. In a preferred embodiment, the system comprises at least two servers, a first server to store and manage a non-structured database, and a second server with previously trained computer program algorithms to process the information stored in the database.

These components are combined to create an architecture for the system that has multiple mobile electronic devices that collect environmental measurements and send them to a database using a gateway. A plurality of users with the mobile application installed on their smartphones publishing new reports and voting on reports about the environmental situation of a place, and plurality of computer readable algorithms installed remotely in servers that gather information from open data sources, store the collected information of all the collecting means and process all the information stored in the database.

The mobile electronic devices measure every T (period for taking measurements) seconds environmental data using the plurality of sensors, and using their geo-location system add a timestamp and a location (i.e., current latitude and longitude) to them, then the mobile electronic devices attempt to send this information using one of their wireless communication interfaces. If none of the two wireless communication interfaces finds another mobile electronic device or a gateway to send the information, it will be stored until the successful transmission of the data.

The multiple electronic devices communicate among themselves via a self-organized, delay, and fault-tolerant communication system that consists of a delay tolerant network (DTN) with a topology of a mobile ad-hoc network. In this network, the mobile electronic devices are not available for communication all the time and are not connected among them all the time either. When they are in an active state they send information stored on their storage unit to another mobile electronic device or a gateway if they are in the coverage zone; otherwise, they store the information and wait to receive information from other mobile electronic devices storing the information collected and received until the mobile electronic device can transmit the data successfully.

The mobile application has two main capabilities: managing the reports sent by users and showing the information services generated by the second server. The "managing the reports" function comprises the way to create a new environmental report, add multimedia files to bring more information about the report and then send it. When the report is sent the application will automatically add the current location of the user and the present time to it. Additionally, the "managing the reports" function comprises the way to allow to a user to see the reports made by other users and vote or comment them. The information services function comprises a way to visualize heat-maps for every source of information, add notifications for environmental alerts, and to have forecasts about the environmental situation of the covered zone.

Finally, the second server takes the information that is stored in the first server, that is the information collected by the mobile electronic devices, the mobile application and the information gathered from open data sources, and takes it as an input of a pre-trained computer program algorithm which will generate an output with information services.

It should further be noted that the information gathered from open data sources is highly reliable environmental information generated by high precision sensors, typically being stationary sensors, installed by local environmental authorities, or by the owner or administrator in indoor spaces. This information is used by the system to continuously calibrate the measurements made by the mobile electronic devices due to the low precision of their sensors. The calibration in the mobile electronic devices is done manually at the first configuration using professional instruments; then the system provides an algorithm for continuously calibrating the sensors based on the measurements collected from high accuracy environmental sensors installed by third parties.

Also, it should be noted that the gateway is connected to the servers by using a virtual private connection over the Internet. Also, the servers are connected to each other using a virtual private link.

FIG. 1 shows the general components of an embodiment of the environmental monitoring system, comprising four main components: a co-creation platform block that collects environmental reports sent by users and allows users to see the reports sent by other users and vote; a sensing on field block that, using mobile electronic devices, takes environmental measurements, an open data sources block that gathers information from open datasets; and a processing system block, which processes information collected by the three aforementioned blocks.

Figure 2:
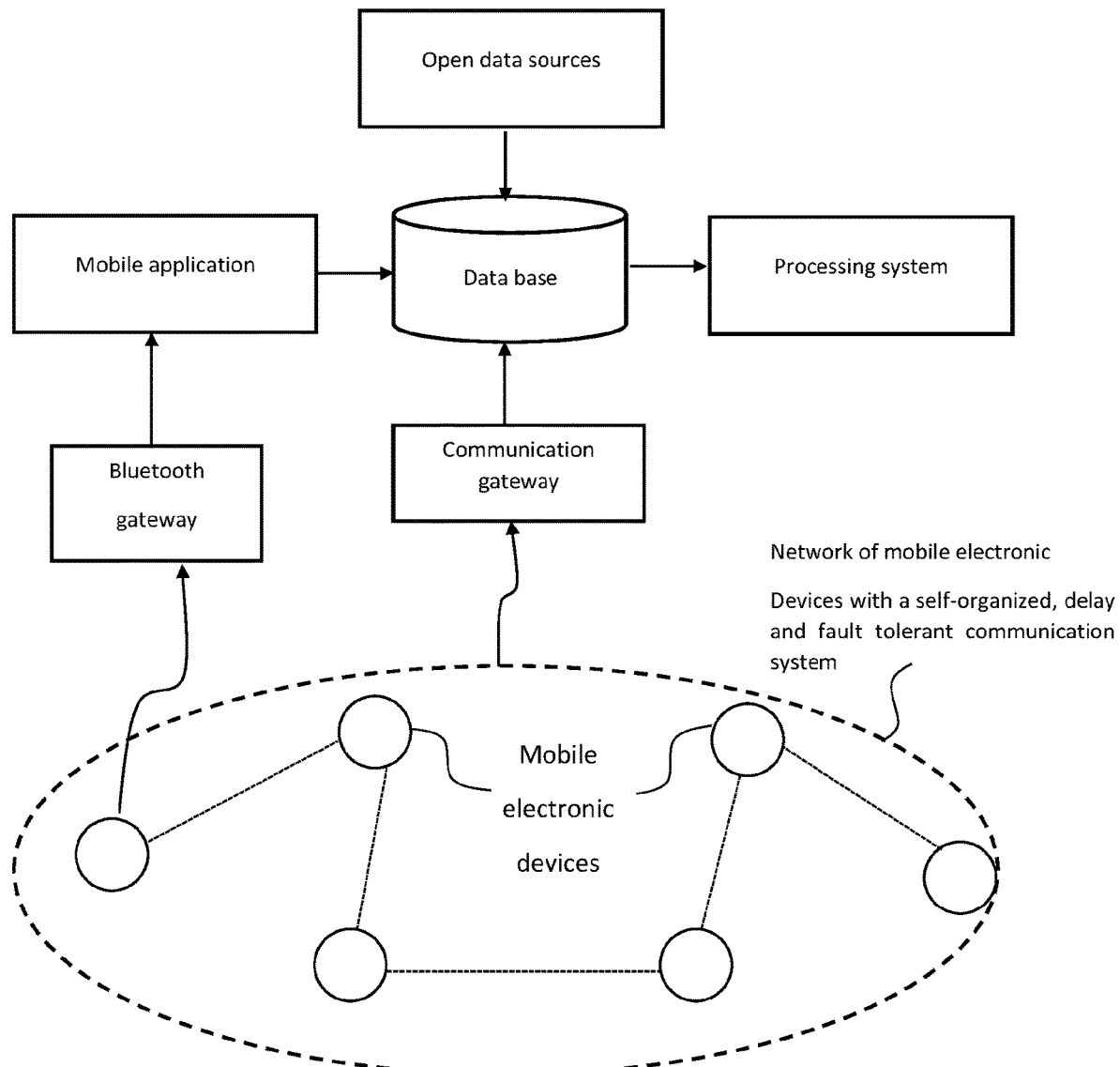
FIG. 2. is an illustration of each component of the system for collecting and processing environmental information based on mobile electronic devices and open data sources according to the present invention.

FIG. 2 shows each component of a preferred embodiment of the system for collecting and processing environmental information. It comprises a wireless network of mobile electronic devices that acquire environmental measurements and send them to the database through a gateway. A mobile application, which is the co-creation platform that collects the information about the environmental reports from the users and sends it to the database using an internet connection. A system for gathering information from open data sources that address the gathered information to the database using an Internet connection. The processing system takes the data stored in the database, and using machine learning algorithms, generates valuable data.

Figure 3:
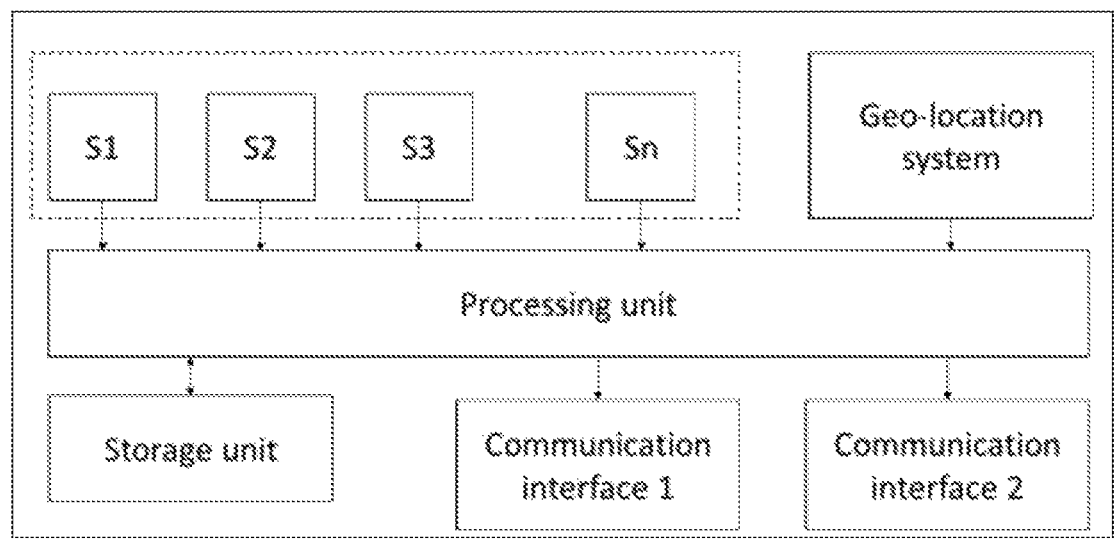
FIG. 3. is an illustration of each component of a mobile electronic device for collecting environmental information according to the present invention.

FIG. 3 shows a mobile electronic device for collecting environmental information used in the present invention. It comprises a plurality of environmental sensors, a geo-location system, a processing unit, a storage unit, and two communication interfaces.

The plurality of sensors measures environmental variables and add a timestamp and a location (latitude and longitude) using the geo-location system. After measurement, this information is sent to the processing unit which attempts to send the data collected and the information already stored on the storage unit through one of the communication interfaces. If the transmission is successful, the stored data will be deleted. Otherwise, the collected information by the plurality of sensors will be stored.

Figure 4:
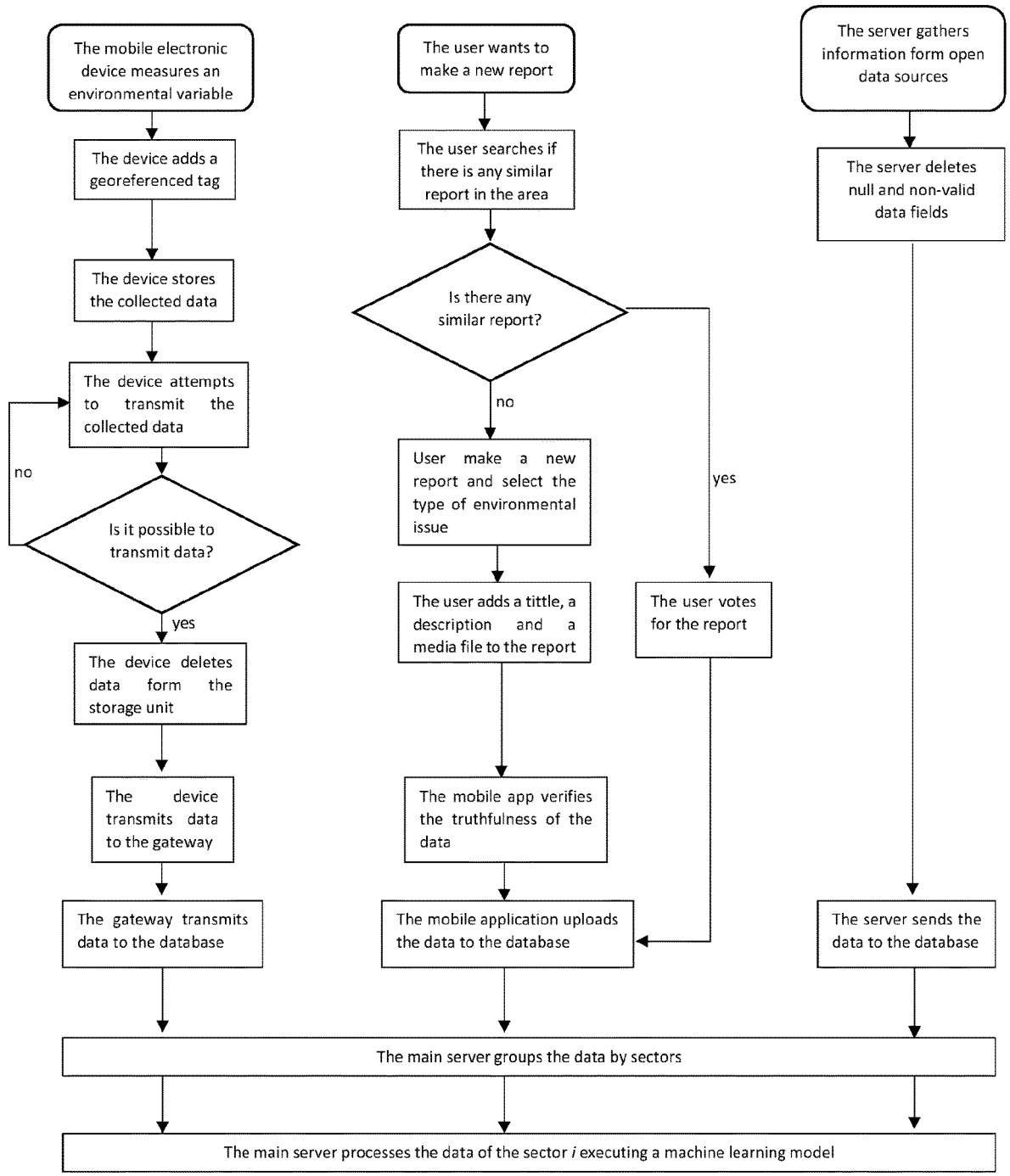
FIG. 4. is an illustration of the different screens of the mobile application for making reports according to the present invention.

FIG. 4 shows the method for determining a level of contamination by collecting and processing data coming from different information sources. For a better understanding of the method, it will be divided into two parts: 1) method for collecting information from various sources and 2) method for combining the collected data.

Each data source has its method of collecting information. Regarding the sensors network, the method is explained as follows. The mobile electronic devices with the plurality of sensors measure environmental variables every T seconds and the geo-positioning system adds a geo-referenced tag and a timestamp to the sensed data. All this information is sent to another mobile electronic device or a communication gateway if it is in the range. Otherwise, the data is stored in the storage unit of the mobile electronic device until the data can be transmitted successfully. The data will be transmitted among mobile electronic devices until the data arrives at the communication gateway. Once the communication gateway receives the data, it will send it to a database. The data sent by the mobile electronic devices contains the mobile electronic device ID, timestamp, geo-reference, and environmental variables with their corresponding measurements. The data is stored in a non-structured database.

Regarding the mobile application, the method is explained as follows. The citizen selects the type of environmental report, then takes a photo, a video, or records an audio file about the report, and writes a short title describing the report and proceeds to uploading. The application automatically adds the current location of the user to the report. This information is sent to the database using a mobile phone Internet connection. Moreover, a user can check if an environmental situation has been reported by another user and vote on it, for example, by indicating that the report is accurate or inaccurate. All of the data about the reports, their votes, and their comments are stored in a collection of the non-structured database. Each report consists of an ID from the person who made the report, name of the report, type of environmental report, geo-reference, number of comments, number of votes, and media file of the report. All of the reports will be pre-processed in order to identify and group those reports that are similar and delete those that are incorrect using custom algorithms that validate data truthfulness in crowdsourcing systems.

All the data collected will be stored in different collections of the non-structured database. This way, users can obtain heat-maps, charts, or timelines in a disaggregated form, i.e., from each information source separately, or in an integrated structure, i.e., combining the data from the different information sources.

Additionally, the mobile application provides supplementary services like the one shown in the following example:

Example 1: Calculation of Healthy Route

The user opens the mobile app and selects the service called "healthy route" and chooses origin and destination.

The mobile application requests calculating a "healthy route" to the processing system by providing the coordinates of the source, the coordinates of the destination and current time.

The processing system receives the incoming information from the mobile application and calculates the possible routes for going from the source coordinates to the destination coordinates.

For each of the possible routes the processing system requests the environmental information of all the zones included in the route from the database and based on the contamination of each zone, the processing system computes a total score for each route.

The processing unit compares the scores of the routes and selects the route with the lowest rating; i.e., the one with the lowest contamination levels.

Moreover, the mobile platform provides other information services like real-time information on pollution levels, historical pollution levels, recommendations, predictions, and feedback reports.

Regarding the method for combining the information coming from different sources, it is explained as follows. First, the processing system will divide the total monitored area into sectors. Each sector will process all types of environmental issues, air pollution, water pollution, soil contamination, noise, among others. For each type of environmental issue, the information stored in the collection of data collected by mobile electronic devices and the information stored in the collection of reports done by residents will be combined using a set of weights and parameters. To be clear, the following example is given:

Example 2: Combining Information about Air Pollution

Step 1: Group the data stored in the database by sectors
Step 2: Take the data of the sector i and make a query filtering the information regarding air pollution.
Step 3: The number of reports in the sector, the number of votes by each report, the measurements are given by the sensor nodes with their timestamps and the historical information is given as input of a pre-trained machine learning model, which will generate pollution alerts and predictions about pollution as output.
Step 4: Based on the pollution alerts generated in step 3, the system will generate a set of recommendations to the residents.

It is important to note that given the large volume of data generated by the information sources, the processing stage should be done using big data techniques in order to guarantee short processing times and provide the information at the right moment.

Figure 5:
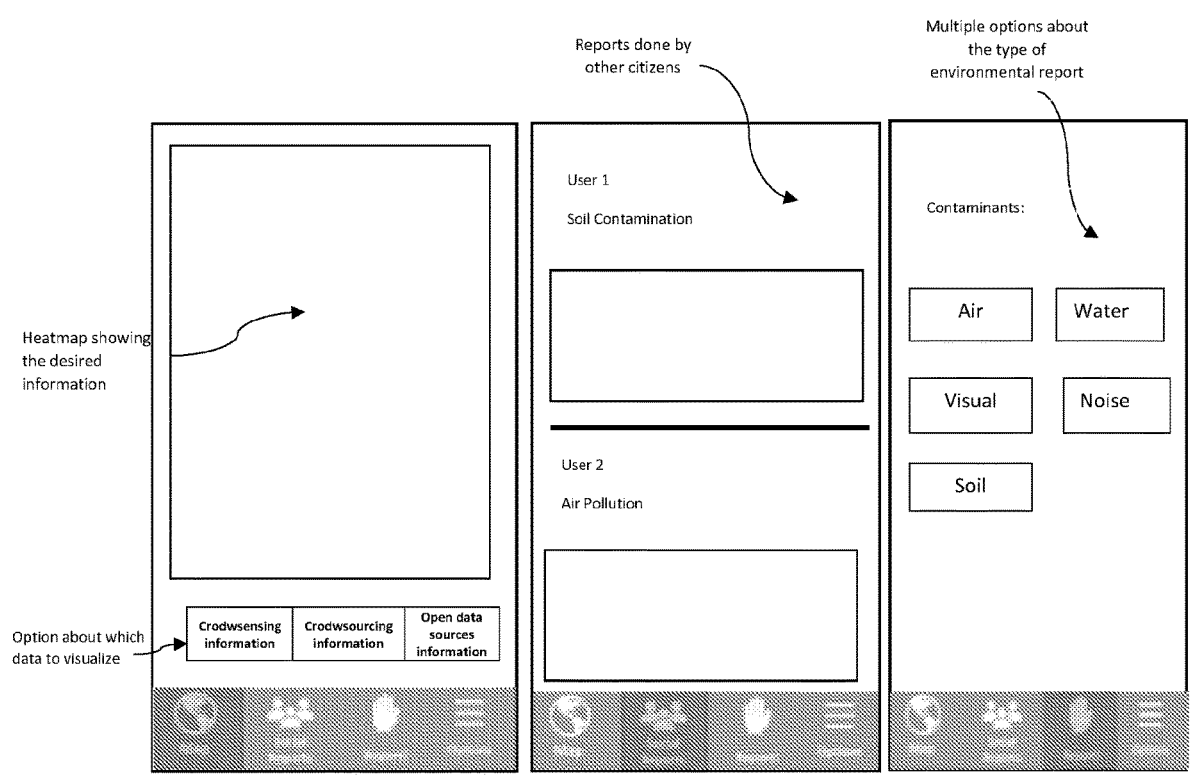
FIG. 5. is an illustration of the algorithm flowchart for collecting and processing the data coming from the sensing nodes, according to the present invention.

FIG. 5 shows the different screens of the mobile application for making environmental reports.

The first screen called "Map" shows a heat-map of the environmental information of the current location and the data shown for the selected options. The heat-map could be generated based only on crowdsensing information (coming from the environmental reports), on crowdsensing information (coming from mobile sensors), on open data sources or on any combination of the sources.

The second screen called "Social reports" shows the reports provided by other users with the name of the report, its votes, and an image about the report. The application gives the user the possibility to vote or comment about any report.

The third screen called "Report!" is the one that allows the user to make environmental reports. As shown in the figure, the first information that is required for the report is the type of contaminant that the user wants to report, and then the name of the report and some multimedia files will be requested.

Different features, variations, and multiple different embodiments have been shown and described with various details. What has been described in this application at times in terms of specific embodiments is done for illustrative purposes only and without the intent to limit or suggest that what has been conceived is only one particular embodiment or specific embodiments. It is to be understood that this disclosure is not limited to any single specific embodiments or enumerated variations, but is limited in scope only by the appended claims. Many modifications, alterations, and other embodiments will come to mind to those skilled in the art, and which are intended to be and are covered by both disclosures. It is indeed intended that the scope of this disclosure should be determined by a proper legal interpretation and construction of the disclosure, including equivalents, as understood by those skilled in the art relying upon the complete disclosure present at the time of filing.

Example 3: System for Measuring the Probability of Transmission of Respiratory Diseases The sensor network measures the air quality in an indoor or an outdoor environment.
The information gathered by the sensor network is stored in a database.
The system accesses to open data sources containing information on the incidence of respiratory disease in the area of the sensor network.
By means of the co-creation app, users can report they are going through a process of respiratory disease.
By means of a machine learning algorithm, the system uses the sensor network information (PM, temperature, humidity, etc.) and the open data sources to calculate a respiratory disease transmission risk index.

Users receive notifications on their co-creation app on the respiratory disease transmission risk index.

Example 4: Integration with Third Party Control Systems

The sensor network measures the environment and sends the data to the network gateway.

The system also integrates open data sources into the data processing system.

The data processing system generates processing data that is used by third party control systems (e.g. an industrial PLC).

In a preferred embodiment, for booting all the components in the mobile electronic system. First, the GPS connection is established, once the signal is received, the system time is set, and DTN protocol and the functions of the system are started.

Now, an example of implementation is showed by a Python code for booting all the components.

```
import os
import time
import datetime
import gpsd
import time
gpsd.connect( )
while true:
   try:
      packet_gps = gpsd.get_current( )
   except (UserWarning):
      print("Starting GPS")
      time.sleep(10)
      continue
   if (packet_gps.mode < 2):
      time.sleep(10)
      print ("NO GPS")
   else:
      os.system("date –s"" + packet gps.time +""" )
      os.system("killall dtnd")
      time.sleep(30)
      os.system("dtnd –l wlan0 –D")
      time.sleep(30)
      os.system("python3.7 UEL_publisher.py")
      break
```

Also, an example of implementation of the map is included for showing the environmental results in the mobile app.

An example of code is included for using an open source library for maps to allow the operation of a map in a simplified way and with optimal performance on different devices.

```
let nbUrl =
'https://api.tiles.mapbox.com/v4/(id}/{z}/{x}/{y}.png?access_token=
pk.eyJ1[joibwfwYn94]iwiYSl6]mNpejY4NXVycTA2enYycX3r
let streets = lesflet.tileLayer(mtUrl, (id: 'mapbox.streets'});
this. map = leaflet.map('nap', {
   center: [latitude, longitude],
   zoom: 12,
   minzoom: 0,
   maxzoom: 50,
   layers: [streets, this.groupCluster]
});
Let baseLayers = {"Reports" : this.groupCluster};
Leaflet.control.layers(baseLayers).addTo(this.map);
```

For the implementation of the map in the mobile application a "leaflet" API is used, which allows the visualization of the map and to draw and filter the points of the places from which the pollutant reports are sent. Also, a geolocation plugin is imported to obtain the real-time location of the user. The following is a code showing an example of implementation of said features:

Ts map.ts ●

Import leaflet from 'leaflet';

Import {Geolocation} from '@ionic-native/geolocation';

Finally, the map component is included in the HTML template of the mobile application, as showed in the code:

```
1    <ion-content>
2
3    <ion-fab class "fab-button" bottom.>
4    <button i o n-fab mini color="light">< ion-icon name="nd-add"></ion- icon></button>
5
6       <ion-fab list side="right">
7          <button i o n-fab (click)= "filterMap( )"><ion icon name="search"></ ion-icon></button>
8          <button i o n-fab (click)= "goToCenter( )"><ion-icon name="md-locate"></ ion-icon></button>
9       <ion-fab-list>
10      <ion-fab>
11
12      <div id="map" style="width:100%; height:100%;">
13      </div>
14
15   </ion-content>
```

Figure 6:
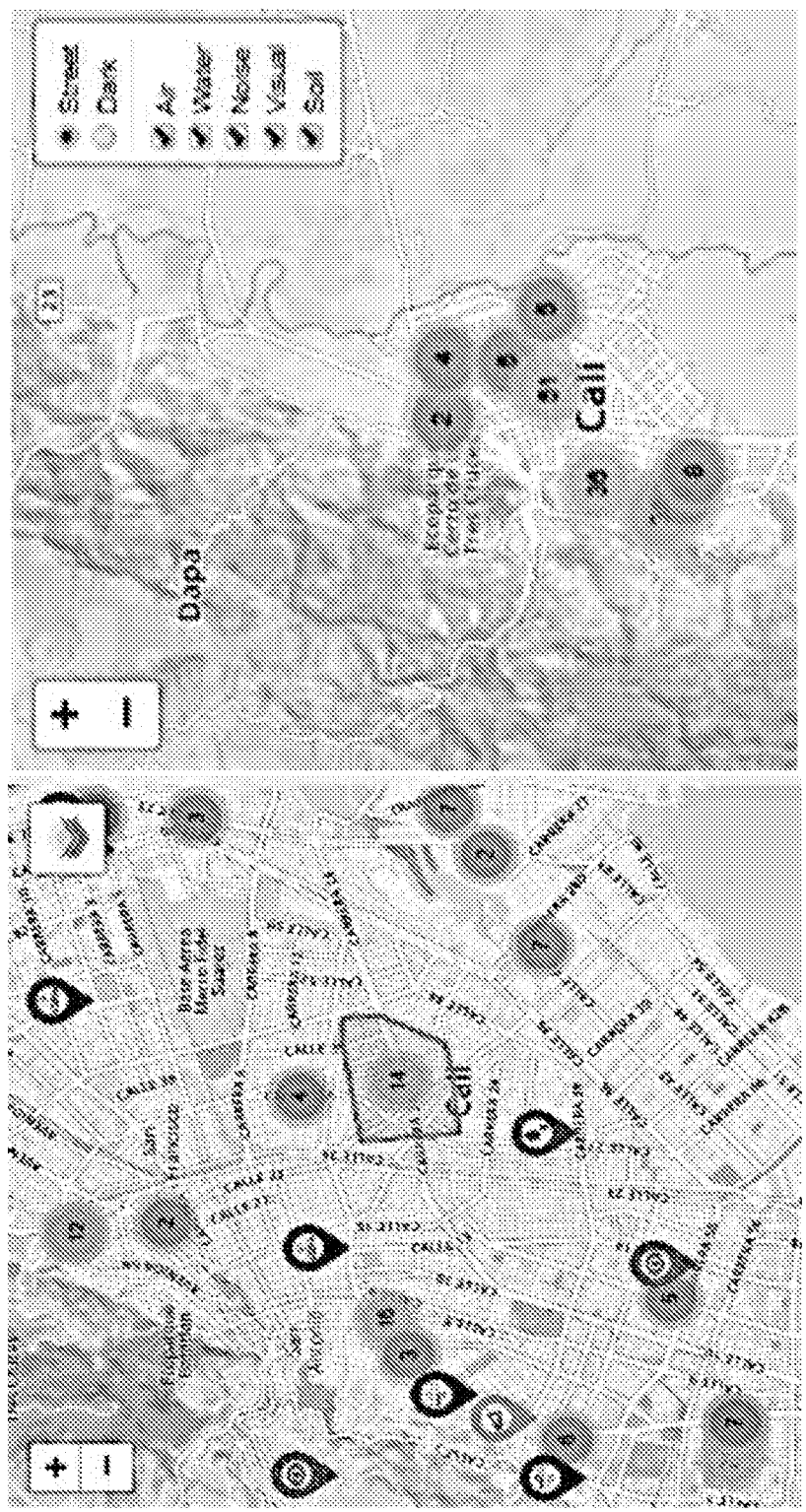
FIG. 6. shows an example of implementation of maps with markers.

FIG. 6 show the implemented maps with markers on it and options to visualize the different types of pollutants.

For the implementation of the report section on the mobile application, two main components were used: the camera plugin and the geo-location plugin, as showed in the following code:

```
                              TS reportts
1    import {Component} from "@angular/core";
2    import {NavController, NavParams, AlertController,
LoadingController, IonicPage} from "ionic-angular";
3
4    /*import plugins*/
5    import {Camera,CameraOptions} from "@ionic-native/camera";
6    import {Diagnostic} from "@ionic-native/diagnostic";
7    import {Geolocation} from "@ionic-native/geolocation";
8
```

The camera plugin is used so that the mobile application can open the camera and take photos according to the configured camera options. The following code shows how the quality of the photo taken is assigned, the type of format, the type of medium to be used and the orientation that the picture should take according to the given approach.

```
initializepreview(selection) {
   /Camera's features*/
   const cameraOptions: CameraOptions = {
      quality: 60,
      destinationType: this.camera.DestinationType.DATA_URL,
      encodingType: this.camera.EncodingType.JPEG
      mediaType: this.camera.MediaType.PICTURE,
      correctOrientation: true,
   };
   /Capture picture*/
   this.camera.getPicture(cameraOptions).then((imagedata) => {
      this.sbImage = "data:image/png;base64," + imageData;
      this.gps( );
   }, (Error) => {
      this.navCtrl.canGoBack( );
   });
}
```

The geo-location plugin, as shown on the following code, is used for the mobile device to capture the user's geo-location and to be able to make information transactions such as sending reports.

```
gps ( ) {
    this.geolocation.getCurrentPosition( ).then((resp) => {
        this.sbLatitude = resp.coorde.latitude;
        this.sbLongitude = resp.coorde.longitude;
    }).catch((error) => {
        this.toast(this.MESSAGE_ERROR_GETTING_GEOLOCATION);
    });
}
```

The invention claimed is:

1. A method for determining the level of contamination in covered zones, comprising:
   providing a server;
   receiving a request to enroll a wireless sensor network (WSN) for measuring a level of contamination as a response to an initial transmission of information from a user reporting contamination issues via a first mobile electronic device;
   attempting to transmit the information to a second mobile electronic device until the first mobile device or the second mobile electronic device obtains a connection to the server, generating a delay-tolerant network (DTN);
   obtaining measured data tagged with a geo-reference tag and a time stamp
   processing the measured data and the information from the user by using big data and machine learning algorithms; and
   providing reports on contamination levels.

2. The method according to claim 1, further comprising obtaining data from open sources.

3. The method according to claim 1, wherein before attempting to transmit the information, the information from the user is processed for determining locations of covered zones where sensors are more needed.

4. The method according to claim 1, wherein the wireless sensor network (WSN) is placed on personal devices or vehicles.

5. The method according to claim 1, wherein the information from users the user is processed for determining truthfulness, by correlating with data reported by other users.

6. The method according to claim 1, wherein providing the reports comprises providing real-time information on contamination levels, historical contamination levels, predictions and contamination alerts or recommendations.

7. The method according to claim 1, wherein a connection between the first mobile device or the second mobile device and the server is performed by a fixed communication gateway or a mobile communication gateway.

8. The method according to claim 1, wherein the measured data and the information from the user are stored in different collections in a non -structured format.

9. The method according to claim 1, wherein the wireless sensor network (WSN) comprises sensors with a certain calibration level, the method further comprising tagging the measured data as a function of the calibration level.

10. The method according to claim 9, further comprising calibrating relatively low-calibrated sensors from the wireless sensor network (WSN) by using data from sensors having a relatively higher level of calibration.

11. The method according to claim 9, further comprising calibrating relatively low-calibrated sensors from the wireless sensor network (WSN) by using data from open sources.

12. A method for transmitting contamination data by using a mobile electronic device, comprising:
   receiving a request from one or more servers to enroll a wireless sensor network (WSN) for measuring level of contamination as a response to an initial transmission of information from a user reporting contamination issues by means of a first mobile electronic device to said one or more servers;
   attempting to transmit such information to second mobile electronic devices until the first mobile device or at least one of the second mobile electronic devices obtains a connection to said one or more servers, generating a delay-tolerant network (DTN); and
   transmitting data tagged with a geo-reference tag and a time stamp measured from sensors of the first mobile electronic device directly, or indirectly, by means of the second mobile electronic devices, to said one or more servers for processing data measured and information from users by using big data and machine learning algorithms, and for providing reports on contamination levels.

13. A system for collecting and processing environmental information, comprising:
   a plurality of mobile electronic devices including a first mobile electronic device and a second mobile electronic device, wherein at least one of the plurality of mobile electronic devices comprises at least one environmental sensor, at least wireless communication interface, a geo -location unit, and a storage unit;
   at least one server configured for storing information obtained from the at least one of the plurality of electronic devices; and
   at least one communication gateway with at least one wireless communication interface and an internet connection configured to receive a request from the at least one server to enroll a wireless sensor network (WSN) for measuring a level of contamination as response to an initial transmission of information from a user reporting contamination issues via the first mobile electronic device, wherein the first mobile electronic device is configured to attempt to transmit the information to the second mobile electronic device until the first mobile electronic device or the second mobile electronic device obtains a connection to the at least one server, generating a delay -tolerant network (DTN), and
   wherein the data tagged with a geo-reference tag and a time stamp measured from sensors of the first mobile electronic device is transmitted directly, or indirectly by means of the second mobile electronic device, to the at least one server for processing data measured and information from users by using big data and machine learning algorithms, and for providing reports on contamination levels.

14. The system of claim 13, wherein the at least one environmental sensor is a temperature sensor, humidity sensor, particulate matter sensor or a gas sensor.

15. The system of claim 14, wherein the gas sensor is selected from one or more of an ozone sensor, a nitrous oxide sensor, a carbon dioxide sensor, a sulfur dioxide sensor, a volatile organic compounds sensor, an ammonia sensor, a hydrogen sulfide sensor, or a carbon monoxide sensor.

16. The system of claim 14, wherein the particulate matter sensor is a PM10 sensor, a PM2.5 sensor, or a PM1.0 sensor.

\* \* \* \* \*